(12) United States Patent
Immaraju et al.

(10) Patent No.: US 9,686,982 B2
(45) Date of Patent: Jun. 27, 2017

(54) TREATMENT OF POTATOES AND ROOT VEGETABLES DURING STORAGE

(71) Applicant: AMVAC CHEMICAL CORPORATION, Newport Beach, VA (US)

(72) Inventors: John A. Immaraju, Newport Beach, VA (US); Anthony A. Zatylny, Newport Beach, VA (US)

(73) Assignee: AMVAC Chemical Corporation, Newport Beach, VA (US)

(*) Notice: Subject to any disclaimer, the term of this patent is extended or adjusted under 35 U.S.C. 154(b) by 0 days.

(21) Appl. No.: 15/340,249

(22) Filed: Nov. 1, 2016

(65) Prior Publication Data

US 2017/0042146 A1    Feb. 16, 2017

Related U.S. Application Data

(62) Division of application No. 14/892,589, filed as application No. PCT/US2014/039054 on May 22, 2014.

(60) Provisional application No. 61/826,309, filed on May 22, 2013.

(51) Int. Cl.
    *A01N 35/00* (2006.01)
    *A01N 35/02* (2006.01)
    *A23B 7/154* (2006.01)
    *A23B 7/152* (2006.01)

(52) U.S. Cl.
    CPC .............. *A01N 35/02* (2013.01); *A23B 7/152* (2013.01); *A23B 7/154* (2013.01); *A23V 2002/00* (2013.01)

(58) Field of Classification Search
    CPC ....................................................... A01N 35/02
    USPC ......................................................... 514/675
    See application file for complete search history.

(56) References Cited

U.S. PATENT DOCUMENTS 9,565,863 B2 * 2/2017 Immaraju .............. A23B 7/022

* cited by examiner

*Primary Examiner* — Nizal Chandrakumar
(74) *Attorney, Agent, or Firm* — Whitham, Curtis & Cook, P.C.

(57) ABSTRACT

The turgidity of potato tubers and other root vegetables is improved, maintained, or restored and/or the greening of potato tubers is delayed, prevented or inhibited and/or internal diseases caused by fungi and bacteria are prevented or treated by the application of one or more α,β-unsaturated aliphatic aldehydes and ketones, C3 to C14 aliphatic aldehydes and ketones, and/or C3 to C7 saturated or unsaturated primary and secondary aliphatic alcohols.

3 Claims, 4 Drawing Sheets

A.

B.

Figure 1 A and B

Figure 3A and B

A.

B.

Figure 4A and B

TREATMENT OF POTATOES AND ROOT VEGETABLES DURING STORAGE

CROSS-REFERENCE TO RELATED APPLICATIONS

This application is a divisional application of U.S. Ser. No. 14/892,589 filed Nov. 20, 2015, now U.S. Pat. No. 9,565,863, which itself was a Rule 371 national stage filing from PCT/US2014/039054 that claimed priority to U.S. Ser. No. 61/826,309 filed May 22, 2013.

BACKGROUND OF THE INVENTION

Field of the Invention

The invention generally relates to maintaining or restoring potato turgidity, and/or to preventing greening and/or to treating interior fungal and bacterial diseases of root vegetables by the application of $\alpha,\beta$-unsaturated aliphatic aldehydes and ketones, C3 to C14 aliphatic aldehydes and ketones, and/or C3 to C7 aliphatic primary and secondary saturated and unsaturated alcohols. In particular, root vegetables (such as potatoes) are treated prior to or during storage to limit damage due to loss of turgidity, greening and/or disease.

Background of the Invention

Following harvest, potato tubers undergo a natural period of dormancy during which sprout growth is inhibited by endogenous hormones. As tubers emerge from dormancy and begin to sprout, respiration increases, starch is catabolized to sugars, which leads to weight loss and loss of turgidity. The result is a decrease in overall quantity and quality of tubers destined for fresh and processing markets. One method to preserve tuber turgidity is to have good sprout control. Hence, efforts have been made to inhibit sprouting through chemical or physical means to preserve quality during storage. The sprout inhibitors registered for use on potatoes in the United States include CIPC (also known as chlorpropham, Sprout Nip®, etc.), maleic hydrazide (MH), DMN (also known as dimethylnaphthalene, 1,4SIGHT®, 1,4SEED®, 1,4SHIP®), DIPN (diisopropylnaphthalene, Amplify®), and clove oil (Biox-C®; Sprout Torch™). Except for MH, which is applied pre-harvest to actively growing plants, all inhibitors are applied post harvest when tubers are in the storage bin.

CIPC is the most effective and most widely used potato sprout inhibitor. This chemical agent is most often applied as a thermal aerosol fog into potato storages after wound-healing and prior to sprouting. In the Pacific Northwest, this is usually in November or December, before dormancy has ended. The chemical is fogged into storage at the recommended rate of 1 lb chlorpropham/600 cwt. One gallon of CIPC aerosol grade will treat 4200 cwt (210 tons) of potatoes. While CIPC can inhibit sprouting and extend the storage life of table-stock and processing potatoes for the storage season with one or more applications, it does not promote or maintain tuber turgidity or prevent tuber greening. One of the drawbacks with CIPC is that when the tubers are treated in storage before proper wound healing and suberization of the potatoes has taken place, CIPC can impede these natural processes and therefore increase storage disease incidence.

While other potential sprout suppressant agents have been identified (e.g. aromatic aldehydes and alcohols, methyl esters of rape oil, carvone, jasmonates, spearmint and peppermint oils), none appear as effective as CIPC. 1,4 SIGHT™ (94.7% DMN=1,4-dimethylnaphthalene) is a naturally-occurring chemical agent that is also registered for sprout control (see U.S. Patent Publication 2001/0021406), but it tends to be less effective than CIPC and is considered a dormancy enhancer.

Other alternative sprout inhibitors are described in U.S. Patent Publication 2007/0135307 to Olson which describes sprout inhibition with carbetamide, pronamide, ethofumesate, mefluidide, paclobutrazol, 2,4 DB, and 2,4 DP, and in U.S. Patent Publication 2007/0078058 which shows the use of MCPP to inhibit sprouting. Issued U.S. Pat. No. 5,139,562 (Vaughn, et al.) discusses the use of the oxygenated monoterpenes 1,4-cineole, 1,8-cineole, fenchone, and menthol to inhibit tuber sprouting.

Other natural volatile sprout inhibitors have been identified. Carvone (derived from caraway seed) is commercially available for use on potatoes in the Netherlands (Hartmans et al 1995. The following US patents describe the use of various compounds for the inhibition of potato sprout formation: U.S. Pat. No. 5,436,226 to Lulai, et al. (Jul. 25, 1995) describes the use of jasmonates; U.S. Pat. No. 5,635,452 to Lulai et al (1997) describes the use of aromatic acids, U.S. Pat. No. 6,855,669 to Knowles and Knowles (2005) describes the use of $\alpha,\beta$ unsaturated aldehydes and ketones, U.S. Pat. No. 8,258,081 to Knowles et al. describes the use of C3 to C14 aliphatic aldehydes, ketones and primary and secondary C3 to C7 aliphatic alcohols to inhibit sprouting of potato tubers, U.S. Pat. No. 5,580,596 to Winkelmann et al. (Dec. 3, 1996) describes the use of rape seed oil and certain long-chain alcohols, either alone or in combination; U.S. Pat. No. 5,139,562 to Vaughn et al., (Aug. 16, 1992) describes the use of volatile monoterpenes (e.g. from eucalyptus, peppermint, spearmint, etc.); and U.S. Pat. No. 8,329,618 B1 teaches that certain essential oils can promote tuber hardness as well, and U.S. Pat. No. 5,129,951 to Vaughn et al., (Jul. 14, 1992) describes the use of aromatic aldehydes and alcohols. In addition, Vokou et al. (1993) have demonstrated that the essential oils from a multitude of herbs (e.g. sage and rosemary) possess sprout inhibiting activity in potatoes.

Softening of the potato during storage significantly decreases or eliminates its commercial value. Thus, identification of agents that can improve turgidity of potatoes are needed in the industry. Furthermore, identification of agents that restore turgidity, whereby an otherwise stored flaccid potatoes absorb moisture and become "hard or firm" to the touch, are of significant commercial interest.

Another possible problem that occurs in association with growing, harvesting and storing potatoes is "greening" which occurs upon exposure to light. Greening adversely affects both the appearance and nutritional qualities—and even the safety—of potatoes, which at one time were considered to be poisonous. In fact potatoes do contain poisonous compounds in the form of glycoalkaloids such as solanine. Such toxins are always present near the surface of the potato, with the highest concentrations in the eyes or sprouts. These toxins are a natural defense mechanism of the plant, and are harmless when ingested in very small quantities, but ingestion of high levels causes headaches, diarrhea, cramps, and, in severe cases, coma and death. The U.S. National Toxicology Program recommends consumption of at most 12.5 mg of solanine from potatoes per day.

Solanine levels in potatoes vary somewhat depending on the variety, age, maturity, storage temperature, etc., but the levels are significantly increased upon exposure to light. Light also causes chlorophyll production and the resulting development of a green skin color; hence, the degree of "potato "greening" is an indirect indicator of the development of toxins such as solanine. Generally, the greener the potato, the more likely that high concentrations of solanine and other glycoalkaloids are present. Commercially grown potatoes are selected so as to have low initial concentrations of solanine, but post-harvest exposure to light can rapidly increase these levels to ten or more times the original value. For example, grocery store fluorescent lighting can induce potato greening in as little as 12 hours. If a potato is more than 5 percent green, the U.S. Department of Agriculture considers the potato damaged and less than US Grade #1.

Unfortunately, there are currently no products available for preventing or slowing "greening" of potatoes and this area is also of significant commercial interest.

In addition, with respect to the treatment of fungal and bacterial diseases in stored produce, it is known that e.g. trans-2-hexenal inhibits mold and bacterial growth on harvested plant commodities (Corbo et al., J. Agric. Food Chem. 48:2401-2408 (2000); Archbold et al., HortScience 34:705-707 (1999)). US patent application 20130266670 (Sardo) teaches that essential oil exhibit fungicidal, bactericidal and/or antioxidative properties. However, these references teach only the control of surface fungal and bacterial pathogens, i.e. the compounds described therein are used as surface sanitizers, whereas diseases that infect the interior of produce (e.g. *Fusarium* dry rot of the potato), and are a huge commercial problem, are not addressed. There is thus still a pressing need in the art to identify and develop agents that prevent, treat, limit and/or cure fungal and bacterial infections (e.g. of root vegetables) that occur within the root itself. Control of such pathogens has significant commercial interest as these pathogens become particularly economically important as they frequently occur during storage. It would be especially desirable to have available agents that can treat and/or eliminate or lessen internal infections that are already present e.g. within a tuber before treatment is begun.

SUMMARY OF THE INVENTION

While treatment of potatoes with certain saturated and unsaturated aldehydes and ketones can be used effectively to control sprouting of potatoes after harvest, it has now been discovered that, in addition, when potato tubers are exposed to these compounds, the exposure has the dramatic effect of maintaining hardness, firmness and/or turgidity of the potatoes, and can even reverse the loss of hardness, firmness and turgidity. The compounds prevent or reverse turgidity loss due to e.g. sprouting and/or general dehydration, thereby improving the overall quality of the tubers as judged by hardening. Increased turgidity also improves the long-term storage of tubers e.g. by reducing pressure bruising in storage due to settling of the potato pile over time. Exposure may be to one individual compound, or to a mixture of two or more compounds, and/or optionally the compound(s) may also be combined with other similar or different beneficial agents.

In addition, these compounds, which include α,β-unsaturated aliphatic aldehydes and ketones, C3 to C14 aliphatic aldehydes and ketones, or C3 to C14 aliphatic primary and secondary saturated and unsaturated alcohols, individually or as mixtures, and alone or in combination with similar or different constituents, have been observed to reduce or prevent greening and to reduce the overall content of glycoalkaloids such as solanine in treated potatoes. Glycoalkaloids are known to be poisonous to both humans and cattle and should not be consumed in significant quantities by either. Therefore, preventing or inhibiting greening of potatoes (i.e., the accumulation of glycoalkaloids in potatoes) is very important to the potato industry, and the use of compositions which incorporate one or more of α,β-unsaturated aliphatic aldehydes and ketones, C3 to C14 aliphatic aldehydes and ketones, or C3 to C14 aliphatic primary and secondary saturated and unsaturated alcohols, alone or in combination, can effectively prevent or inhibit tuber greening.

Further, the present disclosure describes the surprising finding that the compounds described herein are efficacious with respect to preventing and treating infections caused by internal pathogens such as *Fusarium* dry rot, *Pythium* soft rot, *Pythium* leak, Erwinia etc. Internal pathogens enter the potato through the superficial periderm (skin) surface and penetrate the core of e.g. a potato. The present compounds and methods are used to prevent and/or treat such infections, including infections that are well-established prior to treatment.

Thus, tubers which have been subjected to external stresses such as diseases, wounds, exposure to light or generally poor storage conditions can benefit from exposure to the compounds and mixtures thereof as set forth herein.

1. A method for improving, maintaining or restoring potato tuber turgidity, comprising the step of applying to harvested or stored potato tubers, a composition comprising one or more agents selected from the group consisting of: one or more α,β-unsaturated aliphatic aldehydes; one or more α,β-unsaturated aliphatic ketones; one or more C3 to C14 saturated aliphatic aldehydes; one or more C3 to C14 saturated aliphatic ketones; one or more C3 to C14 saturated or unsaturated aliphatic primary alcohols; and one or more C3 to C14 saturated or unsaturated aliphatic secondary alcohols. In some aspects, one or more agents include one or more of 3-decen-2-one, 2-decanone and 2-decanol. In some aspects, the step of applying is performed by fogging or vaporizing. The step of applying may be performed in combination with or sequentially with the application of one or more of: sprout suppressors which are different from said one or more agents, dormancy enhancers, and tuber hardness or firmness enhancers. In some aspects, the one or more agents includes one or more C3 to C14 α,β unsaturated aliphatic aldehydes or C4 to C14 α,β unsaturated aliphatic ketones, and may further include C3 to C14 α,β saturated aliphatic aldehydes or C4 to C14 α,β saturated aliphatic ketones. In some aspects, the harvested or stored potato tubers are already flaccid, prior to application of the agent(s).

The invention also provides methods of inhibiting, delaying or reversing greening of potato tubers, comprising the step of applying to harvested or stored potato tubers, a composition comprising one or more agents selected from the group consisting of: one or more α,β-unsaturated aliphatic aldehydes; one or more α,β-unsaturated aliphatic ketones; one or more C3 to C14 saturated aliphatic aldehydes; one or more C3 to C14 saturated aliphatic ketones; one or more C3 to C14 saturated or unsaturated aliphatic primary alcohols; and one or more C3 to C14 saturated or unsaturated aliphatic secondary alcohols. In some aspects, one or more agents include one or more of 3-decen-2-one, 2-decanone and 2-decanol. In some aspects, the step of applying is performed by fogging or vaporizing. The step of applying may be performed in combination with or sequentially with the application of one or more of: sprout suppressors which are different from said one or more agents, dormancy enhancers, and tuber hardness or firmness enhancers. In some aspects, the one or more agents includes one or more C3 to C14 α,β unsaturated aliphatic aldehydes or C4 to C14 α,β unsaturated aliphatic ketones, and may further include C3 to C14 α,β saturated aliphatic aldehydes or C4 to C14 α,β saturated aliphatic ketones.

The invention also provides methods of preventing or reversing symptoms of a fungal or bacterial infection within potato tubers, comprising the step of applying to harvested or stored potato tubers, a composition comprising one or more agents selected from the group consisting of: one or more α,β-unsaturated aliphatic aldehydes; one or more α,β-unsaturated aliphatic ketones; one or more C3 to C14 saturated aliphatic aldehydes; one or more C3 to C14 saturated aliphatic ketones; one or more C3 to C14 saturated or unsaturated aliphatic primary alcohols; and one or more C3 to C14 saturated or unsaturated aliphatic secondary alcohols. In some aspects, one or more agents include one or more of 3-decen-2-one, 2-decanone and 2-decanol. In some aspects, the step of applying is performed by fogging or vaporizing. The step of applying may be performed in combination with or sequentially with the application of one or more of: sprout suppressors which are different from said one or more agents, dormancy enhancers, and tuber hardness or firmness enhancers. In some aspects, the one or more agents includes one or more C3 to C14 α,β unsaturated aliphatic aldehydes or C4 to C14 α,β unsaturated aliphatic ketones, and may further include C3 to C14 α,β saturated aliphatic aldehydes or C4 to C14 α,β saturated aliphatic ketones. The harvested or stored potato tubers may already exhibit symptoms of one or more fungal or bacterial diseases prior to said step of applying. In some aspects, the fungal or bacterial or disease is *Fusarium* dry rot.

BRIEF DESCRIPTION OF THE DRAWINGS

FIGS. 1A and B. A, potatoes which exhibit excessive sprouting; B, the same potatoes fourteen (14) days after treatment with the alpha-beta unsaturated ketone 3-decen-2-one.

DETAILED DESCRIPTION OF THE PREFERRED EMBODIMENTS OF THE INVENTION

As shown in the Examples provided below, treating harvested and stored potatoes with one or more of α,β-unsaturated aliphatic aldehydes and ketones, C3 to C14 aliphatic aldehydes and ketones, or C3 to C7 aliphatic primary and secondary saturated and unsaturated alcohols, alone or in combination, has been found to effectively maintain, improve, or restore potato turgidity, to prevent potato greening and to mitigate symptoms of internal disease. In other words, the compounds are used as anti fungal and antibacterial agents. These compounds have previously been used to suppress potato tuber sprouting and are discussed in detail in U.S. Pat. No. 6,855,669 and U.S. Pat. No. 8,258,081 both of which are herein incorporated by reference.

The mechanism of action behind the observations presented herein is not precisely known, but, without being bound by theory, the hypothesis is that 3-decen-2-one stopped and reversed the water loss from the potato tubers, and prepared the tubers to absorb moisture and restore firmness during storage in the relatively high humidity facility. This would likely occur through absorption of moisture through the vascular periderm or through the selective opening and closing of lenticels on the tubers. In addition, 3-decen-2-one likely simultaneously shut down moisture loss by destroying sprout tissue and suberization of the sprout attachment site. 3-decen-2-one treatment likely also reduced the respiration rate of the tubers to below that of sprouting tubers, the net result being that turgidity was restored, greening was prevented, and symptoms of disease were reversed or arrested.

Based on these observations, application to root vegetables such as potato tubers of one or more α,β-unsaturated aliphatic aldehydes and ketones, C3 to C14 aliphatic aldehydes and ketones, or C3 to C14 aliphatic primary and secondary saturated and unsaturated alcohols, alone or in combination with each other and/or other constituents, is used to increase tuber turgidity or hardness during storage, and to reduce the potato greening problem associated with glycoalkaloid formation, and to control the development of fungal andbacterial diseases. The root vegetables may or may not have broken dormancy and may or may not be sprouting to benefit from such treatment.

The following terms and definitions are used herein:
By "turgidity" or "hardness" or "firmness" we mean the ability of the potato tuber to retain water content at sufficient levels and maintain a high bulk density. Those of skill in the art will recognize that measurements of "firmness", which is generally expressed as Newtons, varies depending on the type or variety of tuber or vegetable being measured, the particular batch of vegetables, on the instrument being used, and when a measurement is taken (e.g. earlier or later in the growing season). Further, "firmness" measurements may increase during storage due e.g. to water loss which increases the force needed to penetrate the outer surface of the potato, even though the potato is by observation and handling, less firm and more flexible. Thus, firmness is generally analyzed in comparison to a control measurement taken, for example, in a postharvest (but prior to or early in storage) control sample. For example, a tuber treated as described herein will typically exhibit a firmness that is at least about 1, 2, 3, 4, or 5% higher than a similar control tuber that has not been so treated, but which has been otherwise kept in the same conditions with respect to storage, e.g. same temperature, humidity, etc. The % increase is, for example, about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0% (or more) compared to control potatoes that have not been treated as described herein. Such a percentage decrease may be considered to represent or accord with a transition from a "firm" to a "flaccid" state (e.g. see, for example, Arvanitoyannis et al, Int J of Food Sci 2008, 43, 1960-1970; and Foukaraki et al. Proc. XXVIIIth IHC-IS on Postharvest Technology in the Global Market, eds Cantwall and Almeida Act Hort 934, ISHS 2012, and references cited therein). Turgidity (turgor) is measured using a suitable calibrated instrument, several of which are known in the art (e.g. Stable Micro System (SMS) instruments such as the TA-XT-2 texture analyzer, the Magness-Taylor pressure tester, the Effegi tester, Fruit Firmness Tester-FFF-Series, Cantifruit tester, AGROSTA®14 Field, FirmTech1, Low Mass Impactor, Instron, and various penetrometers (e.g. the PCE-PTR 200 Penetrometer), and nondestructive mechanical sensors such as those described in U.S. Pat. No. 6,375,999, the complete contents of which is hereby incorporated by referenced in entirety, etc. While the absolute measurements with each type of equipment can vary due to design, the relative numbers for turgid vs non turgid (expressed as a percentage) generally remain the same, or at least within the range of experimental error (e.g. 10% or less), regardless of the instrument used.

Alternatively, or in addition, specific gravity may be used as a measure of the solids in tubers. Generally speaking, on average, potatoes contain about 78% water and 22% dry matter or solids. However, potatoes can range from a 1.060 specific gravity (16.0% dry matter) to over 1.100 (24.4% dry matter), and even very small changes in specific gravity have a large impact on the culinary qualities of a potato. Potatoes with high specific gravity, i.e. greater than 1.08, will make a dry, fluffy baked potato, but will fall apart quickly into mush when boiled. Thus, for potatoes, a satisfactory specific gravity for baking or mashing is considered to be at least 1.08. Lower dry matter potatoes, e.g. specific gravity between 1.08 and 1.07, will remain firm when boiled, but will make a very wet, waxy baked potato (see the website located at tuckertater.com/potato-glossary). Potatoes with a specific gravity below 1.07 may be acceptable for frying, but generally, if specific gravity is less than about 1.07, the potatoes will not meet the standards maintained in the industry for other purposes. Those of skill in the art will recognize that specific gravity can be measured by weighing a sample of potatoes in air and then re-weighing in water. The specific gravity can then be determined using the following formula: specific gravity=(weight in air) divided by [(weight in air)−(weight in water). For example, if the potato weight in air (g)=935.95 and the weight in water (g)=80.13, then the specific gravity=1.094.

"Tuber hardness or firmness enhancers" refers to agents that increase the turgidity of root vegetables such as potato tubers, for example, dimethyl naphthalene which can be used together with the above compounds.

By "dormancy enhancer" we mean an agent that induces or promotes dormancy in a potato tuber or other root vegetable, such as dimethyl naphthalene (U.S. Pat. No. 6,375,999 (Forsythe), the complete contents of which are hereby incorporated by reference in entirety.)

"Sprout inhibitors" refers to agents, including those described herein, that decrease the amount or the rate of development of sprouts on harvested or stored root vegetables such as potatoes, for example, chlorpropham (CIPC), clove oil, mint oil, dimethyl naphthalene, diisopropyl naphthalene, maleic hydrazide etc.

"Root vegetables" as used herein refers to various edible true roots such as tuberous roots and taproots, as well as non-roots such as tubers, rhizomes, corms, and bulbs (see below).

As used herein "adjuvant" refers to any compound which enhances the penetration through the skin of the tuber of the compounds described herein or assists with the spread of the same on top of the skin of the tuber. Examples of suitable adjuvants include but are not limited to various surfactants, oils and other inorganic and organic compounds, e.g. Hasten®, Agridex®, various organosilicone adjuvants (e.g. Pulse®), various non-ionic wetting agents, etc.

Suitable C3 to C14 $\alpha,\beta$-unsaturated aldehydes and ketones for use in the methods of the invention are described in U.S. Pat. No. 6,855,669, the complete contents of which are hereby incorporated by reference. Suitable C3 to C14 aliphatic aldehydes and ketones and C3 to C4 aliphatic saturated or unsaturated primary and secondary alcohols (which are metabolites of C3 to C14 $\alpha,\beta$-unsaturated aldehydes and ketones) are described in co-pending U.S. patent application Ser. No. 12/186,861 (published as US 2009-0062126, the complete contents of which are hereby incorporated by reference) and U.S. Pat. No. 8,258,081 (the complete contents of which are hereby incorporated by reference). The metabolites may be applied directly to root vegetables as "first components", or indirectly as a result of the application of C3 to C14 $\alpha,\beta$-unsaturated aldehydes and ketones parent compounds, the metabolites appearing on the vegetables as breakdown products.

The methods of treating root vegetables described herein may involve (include) a step of identifying root vegetables that can benefit from such treatment. Exemplary root vegetables include those that are have been harvested, those that are being or have been loaded and/or transported, those that are being stored prior to distribution to stores or consumers, and those that have been distributed (made available) to an end user, e.g. a restaurant, a processing facility (e.g. canning, frozen food, juice, etc. facility), or an individual consumer. In particular, the root vegetables may already exhibit one or more undesirable characteristics such as sprouting, loss of turgidity and firmness, and/or evidence of disease, such as disease at the interior of the potato. Symptoms of interior diseases occur inside the potato, for example, at least about 1-2 mm beyond (beneath) the skin (periderm), or at least about 1-10 mm, or about 1-5 cm or more beyond, depending on the size and dimensions of the potato. Such infections are thus present in the fleshy portion or core of the potato, the part of the potato that is encased by skin. However, such infections may also involve, breach or damage the skin.

The treatment of root vegetables may be carried out by any suitable method known to those of skill in the art, For example, by simultaneous fogging from one or a plurality of sources (e.g. by cold or thermal including thermal-electric, internal combustion or gas fired methods); by direct spraying (e.g., when formulated to be diluted in water); or by misting or humidification systems or other commercially available applications systems; or via tank mixed, co-injections from multiple or separate injection systems into the same applicator or application system; or by deposition or release from slow-release matrices which may be added to or incorporated in plastic, paper, or box materials used to store the tubers etc. The amount of the one or more $\alpha,\beta$-unsaturated aliphatic aldehydes and ketones, C3 to C14 aliphatic aldehydes and ketones, or C3 to C14 aliphatic primary and secondary saturated and unsaturated alcohols, applied to the potato tubers can vary depending on the application mode, storage requirements, and other factors, however, it is exposure of the potato tubers to an amount ranging from 0.01 mmol to 5.0 mmol will be sufficient to have the desired effect. For turgidity, commercially available pressure testing devices which measure firmness or hardness can be used to guide adjustments in application regimens for different storage lots. The applications can be made a single time or multiple times over the course of one or several seasons. For example, beneficial effects (e.g. in terms of improving, maintaining or restoring turgidity) may result with two applications, where one application is made a few weeks (e.g. 2-8 weeks) after the vegetables have been transferred post-harvest into storage, and a second application is made after a time interval of from about 30-45 days. Similarly exposure of the vegetables to an amount of the one or more $\alpha,\beta$-unsaturated aliphatic aldehydes and ketones, C3 to C14 aliphatic aldehydes and ketones, or C3 to C14 aliphatic primary and secondary saturated and unsaturated alcohols, ranging from 0.01 mmol to 5.0 mmol will be suitable to cause a reduction of an accumulation of glycoalkaloid, such as solanin, content in tubers (thus reducing or inhibiting undesirable potato greening); and to combat disease within or among the stored vegetables.

The application window for the one or more α,β-unsaturated aliphatic aldehydes and ketones, C3 to C14 aliphatic aldehydes and ketones, or C3 to C17 aliphatic primary and secondary saturated and unsaturated alcohols, applied to the potato tubers is, for example, at the time of storage (e.g. within minutes or a few hours, e.g. 1-24 hours of the potatoes being introduced into a storage container) or from about one to a few days after the vegetables have been stored, and/or anytime thereafter up to about 24 hours prior to the unloading from storage. An exemplary time frame during which stored potatoes can be treated ranges from a few days post-storage (e.g. after about 1, 2, 3, 4, 5, 6, 7, 8, 9 or 10 days after the potatoes are introduced into a storage container) up to several months (e.g. about 1, 2, 3, 4, 5, 6, 7, 8, 9, or 10 months) in storage. Application/exposure may occur at any time or after any period of time when the potato tubers are susceptible to pile settling.

The one or more α,β-unsaturated aliphatic aldehydes and ketones, C3 to C14 aliphatic aldehydes and ketones, or C3 to C14 aliphatic primary and secondary saturated and to unsaturated alcohols, applied to the vegetables, can be applied in combination with other compounds, including but not limited to sprout suppressants (e.g., CIPC, DMN, DIPN, mint oil, carvone, clove oil, carbetamide, pronamide, ethofumesate, mefluidide, paclobutrazol, 2,4 DB, 2,4 DP, or maleic hydrazide (MH)), dormancy enhancers, tuber hardness enhancers, or adjuvants. These ingredients can be tank mixed or applied sequentially. The one or more α,β-unsaturated aliphatic aldehydes and ketones, C3 to C14 aliphatic aldehydes and ketones, or C3 to C14 aliphatic primary and secondary saturated and unsaturated alcohols, applied to the potato tubers may include a plurality of these agents, e.g., 2, 3, 4, 5, 6, 7, 8, 10, 12 or more, or even 15, 20, 25, or 30 or more, without limitation.

Exemplary aliphatic C3 to C14 aldehydes that may be used in the practice of the invention generally have the chemical formula where $R_1$ is a C2 to C13 branched or unbranched, substituted or unsubstituted saturated alkyl or a C2 to C13 branched or unbranched, substituted or unsubstituted unsaturated alkenyl. In some embodiments of the invention, the aldehyde is nonanal, or decanal,

Exemplary aliphatic C3 to C14 ketones that may be used in the practice of the invention generally have the chemical formula where $R_2$ and $R_3$ are C1 to C12 branched or unbranched, substituted or unsubstituted saturated alkyl or a C1 to C12 branched or unbranched, substituted or unsubstituted unsaturated alkenyl. $R_2$ and $R_3$ may be the same or different. The sum of the carbons in $R_2+R_3$ does not exceed 13. In some embodiments of the invention, the ketone is 2-nonanone, or 2-decanone, Exemplary agents which may be used in the practice of this invention include one or more C3 to C14 αβ unsaturated aliphatic aldehydes or C4 to C14 αβ unsaturated aliphatic ketones, as are described by example in U.S. Pat. No. 6,855,669 to Knowles et al., which is herein incorporated by reference. The aliphatic aldehydes and ketones are defined by general formulas I and II, respectively:

Formula I

Formula II where
$R_1$ is H or branched or unbranched, substituted or unsubstituted $C_1$-$C_{11}$ lower alkyl, or branched or unbranched, substituted or unsubstituted $C_1$-$C_{11}$ lower alkenyl;
$R_2$ is branched or unbranched, substituted or unsubstituted $C_1$-$C_{11}$ lower alkyl, or branched or unbranched, substituted or unsubstituted $C_1$-$C_{11}$ lower alkenyl; and
$R_3$ is H or branched or unbranched, substituted or unsubstituted $C_1$-$C_{10}$ lower alkyl, or branched or unbranched, substituted or unsubstituted $C_1$-$C_{10}$ lower alkenyl.

As discussed above, very good results have been achieved with 3-decen-2-one. Exemplary more C3 to C14 αβ unsaturated aliphatic aldehydes or C4 to C14 αβ aliphatic ketones include trans-2-pentenal, trans-2-hexenal, trans-2-heptenal, trans-2-octenal, trans-2-nonenal, trans-2-decenal, trans-2-undecenal, trans-2-dodecenal, trans-2,4,-nonadienal, trans-2, cis-6-nonadienal, and trans-3-nonen-2-one.

Exemplary aliphatic C3 to C14 primary alcohols that may be used in the practice of the invention generally have the chemical formula where $R_4$ is a C2 to C6 branched or unbranched, substituted or unsubstituted saturated alkyl or a C2 to C6 branched or unbranched, substituted or unsubstituted unsaturated alkenyl. In various embodiments of the invention, the unsaturated C3 to C14 primary alcohol is 1-hexanol,

1-hexanol 1-heptanol,

1-hexanol trans-2-hexen-1-ol, trans-2-hexen-1-ol or trans-2-hepten-1-ol, or trans-2-hexen-1-ol

Exemplary aliphatic C3 to C14 secondary alcohols that may be used in the practice of the present invention generally have the chemical formula where $R_5$ and $R_6$ is a C1 to C5 branched or unbranched, substituted or unsubstituted saturated alkyl or a C1 to C5 branched or unbranched, substituted or unsubstituted unsaturated alkenyl. The sum of the carbons in $R_5+R_6$ does not exceed 6 $R_5$ and $R_6$ may be the same or different. In one embodiment of the invention, the saturated C3 to C14 secondary alcohol is 2-heptanol, In addition, various C3 to C14 primary and secondary alcohols may be used in the practice of the invention. These compounds may be provided directly or may be provided via the breakdown of α,β-unsaturated aliphatic aldehydes and/or α,β-unsaturated aliphatic ketones as described herein. C3 to C14 primary alcohols have the general formula Where $R_7$ is a C3 to C13 branched or unbranched, substituted or unsubstituted saturated alkyl or a C3 to C13 branched or unbranched, substituted or unsubstituted unsaturated alkenyl.

C3 to C14 secondary alcohols have the general formula where R8 is a C1 to C12 branched or unbranched, substituted or unsubstituted saturated alkyl or a C1 to C12 branched or unbranched, substituted or unsubstituted unsaturated alkenyl; and R9 is a C1 to C12 branched or unbranched, substituted or unsubstituted saturated alkyl or a C1 to C12 branched or unbranched, substituted or unsubstituted unsaturated alkenyl. The sum of R8 and R9 is not less than 3 and does not exceed 13.

Examples of additional compounds that may be used in the practice of the invention include but are not limited to the following:

Exemplary aliphatic C3 to C14 aldehydes that may be used in the practice of the present invention include but are not limited to: propanal, butanal, pentanal, hexanal, heptanal, octanal, 4-nonenal, 6-nonenal, decanal, undecanal, dodecanal, tridecanal, and tetradecanal.

Exemplary aliphatic C3 to C14 ketones that may be used in the practice of the present invention include but are not limited to: propanone, 2-butanone, 2-pentanone, 2-hexanone, 2-heptanone, 2-octanone, 3-octanone, 3-nonanone, 2-decanone, 3-decanone, 2-undecanone, 2-dodecanone, 2-tridecanone, 2-tetradecanone, and 3-decen-2-one.

Exemplary aliphatic C3 to C14 primary alcohols that may be used in the practice of the present invention include but are not limited to: 1-propanol, 1-butanol, 2-buten-1-ol, 1-pentanol, 2-penten-1-ol, 1-hexanol, 2-hexen-1-ol, and 1-heptanol.

Exemplary aliphatic C3 to C14 secondary alcohols that may be used in the practice of the present invention include but are not limited to: 2-propanol, 2-butanol, 2-pentanol, and 2-hexanol.

Exemplary aliphatic C3 to 14 primary alcohols that may be used in the practice of the present invention include but are not limited to: 1-octanol, 1-decanol and 2-nonen-1-ol.

Exemplary aliphatic C3 to C14 secondary alcohols that may be used in the practice of the present invention include but are not limited to: 2-octanol, 2-nonanol, and 2-decanol By "substituted" it is meant that there is a replacement of one or more hydrogens with a monovalent or divalent radical. Suitable substitution groups include but are not limited to, for example, hydroxyl, nitro, amino, imino, cyano, halo, thio, thioamido, amidino, imidino, oxo, oxamidino, methoxamidino, guanidino, sulfonamido, carboxyl, formyl, lower alkyl, halo-lower alkyl, lower alkoxy, halo-lower alkoxy, lower alkoxyalkyl, alkylcarbonyl, cycloalkyl, heterocycloalkyl, alkylthio, aminoalkyl, cyanoalkyl, and the like.

In practice, it is expected that application will typically be made to bulk produce in storage bins, although this need not be the case as the compounds may be applied to produce stored or sorted in any manner, so long as sufficient contact is made between the compounds and the produce to improve, maintain, or restore turgidity, prevent greening and the consequent, or concomitant, production of glycoalkaloids, and to thwart disease symptoms. Application of the compounds may be carried out by any of several methods. Generally, the compound(s) will be volatilized, e.g. by cold fogging, or at high temperature (or hot fogging, which utilize various heat sources such as gasoline, propane, butane, natural gas, electric, etc.) to create a thermal fog, or by atomization, and introduced into storage bins e.g. via the ventilation or humidification system. This introduction may be a discrete event that is carried out once or multiple times throughout the storage period. Alternatively, a slow-release mechanism or formulation may be employed in which the compound gradually enters the storage area over a longer period of time, for example by evaporation from a source impregnated with the compound(s). Further, the compounds may also be advantageously applied by spraying or misting a liquid form of the compound onto the vegetables, or by dipping or otherwise coating them with the compound, either prior to, during, or after storage (e.g. between storage and boxing or bagging for commercial purposes). Such compounds can also be used to coat or impregnate consumer containers (such as cardboard boxes, burlap bags, plastic bags, etc.) which typically hold root vegetables coming out of storage sheds or bins for the express purpose of making available the precursor or metabolite compounds to maintain turgidity, delay greening and prevent storage fungal and bacterial diseases in transit and at final destinations (e.g. homes, grocery stores, restaurants and other food establishments). For such applications, the compounds may also be mixed with various other agents known to facilitate the delivery of gases, liquids, or gels as appropriate (e.g. emulsifiers, slow release agents or matrices and the like). Other means of delivering the one or more include but are not limited to employing tank mixtures of the combination of inhibitors. Any delivery method known in the art may be used. The application of the compounds (including mixtures) may be carried out only once as described above (i.e. early in storage and before or after sprouting). Alternatively, depending on the factors such as the cultivar, the time of harvest, the length of storage, the intended use, etc. multiple applications of the compound(s) may be made. However, if storage is long term (e.g. over the entire winter for distribution in the spring or the following summer) multiple applications may need to be made. In an exemplary case, the first application will generally be made early in the storage process (e.g. at between 2 and 32 weeks following harvest), and subsequent applications may also be made at roughly 4 to 12 week intervals as needed, until the produce is retrieved for use.

The amount of compound (or compounds) which is (or are) applied is sufficient to terminate, slow, prevent, and/or maintain, improve, or restore a desired trait, e.g. turgidity of the potato tubers, and/or to prevent or inhibit greening of the potato tubers, and/or to prevent, reduce or treat storage-related diseases. Greening of the potatoes and/or decreases in turgidity and/or disease symptoms may be prevented altogether, or be delayed, or slowed compared to untreated tubers, etc. In any case, the process of greening and/or the process of turgidity loss and/or disease development is inhibited or slowed by treating the potato tubers with the compounds as described herein, or with their precursor compounds (e.g. see U.S. Pat. No. 6,855,669, for examples of precursor α,β-unsaturated aldehydes and ketones which can be used to make the ketones and aldehydes and alcohols of this invention), in comparison to potato tubers that are not exposed to or contacted by the compounds in a similar manner. The decrease will be in the range of at least about 10 to 100%, preferably in the range of about 50 to 100%, and most preferably in the range of about 75 to 100%. Thus, the treated tubers will display a decrease in greening development or turgidity reduction of about 10, 20, 30, 40, 50, 60, 70, 80 90, or 100%, compared to untreated tubers. The beneficial effects generally last between 14 and 100 days and in some cases as much as six months depending on storage temperature and other conditions.

Similarly, the presence of fungal and/or bacterial diseases may be prevented or treated by applying the compounds as described herein, either before or after disease symptoms develop. In some cases, loss of turgidity, greening and/or symptoms of disease, are completely prevented (prophylactically) before symptoms occur, or are reversed or eradicated, if symptoms are already present before application. However, those of skill in the art will recognize that the results can also be highly beneficial even if some symptoms (or some greening, or loss of turgidity) remain(s) or eventually develop(s), i.e. even if the progress of the development of unwanted characteristics is arrested (but not reversed), slowed, decreased, lessened, or delayed, or if the amount or extent of damage is decreased, but not completely eliminated.

Types of produce that may be treated as described herein include but are not limited to: root vegetables categorized as i) true roots (e.g. *Cassava tuberous* roots);

ii) taproots [*Arracacia xanthorrhiza* (arracacha), *Abelmoschus moschatus* (bush carrot); *Beta vulgaris* (beet and mangelwurzel), *Brassica* spp. (rutabaga and turnip), *Bunium persicum* (black cumin), Burdock (*Arctium*, family Asteraceae), Carrot (*Daucus carota* subsp. *sativus*), Celeriac—(*Apium graveolens rapaceum*), Daikon—East Asian radish (*Raphanus sativus* var. *longipinnatus*), Dandelion—(*Taraxacum*) spp., *Lepidium meyenii* (maca), *Microseris scapigera* (yam daisy), *Pachyrhizus* spp. (jicama and ahipa), Parsnip (*Pastinaca sativa*), *Petroselinum* spp. (parsley root), Radish—(*Raphanus sativus*), *Scorzonera hispanica* (black salsify), *Slum sisarum* (skirret), *Tragopogon* spp. (salsify), *Vigna lanceolata* (bush potato), etc.]

iii) tuberous roots [*Amorphophallus galbra* (Yellow lily yam), *Conopodium majus* (pignut or earthnut), *Dioscorea opposita* (nagaimo, Chinese yam, Korean yam), *Hornstedtia scottiana* (Native ginger), *Ipomoea batatas* (sweet potato), *Ipomoea costata* (desert yam), *Manihot esculenta* (cassava or yuca or manioc), *Mirabilis extensa* (mauka or chago), *Psoralea esculenta* (breadroot, tipsin, or prairie turnip. *Smallanthus sonchifolius* (yacóon), etc.]

iv) root-like stems, e.g. *Zamia pumila*, Florida arrowroot v) modified plant stems e.g. Taro corms, Ginger rhizomes, Yam tubers vi) corms such as *Amorphophallus konjac* (konjac), *Colocasia esculenta* (taro), *Eleocharis dulcis* (Chinese water chestnut), *Ensete* spp. (enset), *Nelumbo nucifera, Nymphaea* spp. (waterlily), *Pteridium esculentum, Sagittaria* spp. (arrowhead or wapatoo), *Typha* spp., *Xanthosoma* spp. (malanga, cocoyam, tannia, and other names), etc.

vii) rhizomes such as *Curcuma longa* (turmeric), *Panax ginseng* (ginseng), *Arthropodium* spp. (rengarenga, vanilla lily, and others), *Canna* spp. (*canna*), *Cordyline fruticosa* (ti), *Maranta arundinacea* (arrowroot), *Nelumbo nucifora* (lotus root), *Typha* spp. (cattail or bulrush), *Zingiber officinale* (ginger, galangal), etc.

viii) tubers such as *Apios americana* (hog potato or groundnut), *Cyperus esculentus* (tigernut or chufa), *Dioscorea* spp. (yams, ube), *Helianthus tuberosus* (Jerusalem artichoke or sunchoke), *Hemerocallis* spp. (daylily), *Lathyrus tuberosus* (earthnut pea), *Oxalis tuberosa* (oca or New Zealand yam), *Plectranthus edulis* and *P. esculentus* (kembili, dazo, and others), *Solanum tuberosum* (potato), *Stachys affinis* (Chinese artichoke or crosne), *Tropaeolum tuberosum* (mashua or añu), *Ullucus tuberosus* (ulluco), etc.

ix) bulbs such as Shallot bulbs, *Allium* spp. (garlic, onion, shallot, et cetera), *Camassia quamash* (quamash), *Cyperus bulbosus* (bush onion), *Caladenia, Cryptostylis, Cymbidium canaliculatum, Diuris, Dipodium, Erythronium* spp. (katakuri), *Foeniculum vulgare* (fennel), *Geodorum, Glossodia, Lilium* spp. (lilies), *Lypernathus, Microtis, Prasophyllum, Pterostyli, Tacca leontopetaloides, Thelymitra*, etc.

Diseases that may be addressed or treated using the compounds and methods described herein include but are not limited to:

i) fungal diseases such as Black dot (*Colletotrichum coccodes, Colletotrichum atramentarium*), Brown spot and Black pit (*Alternaria alternate, Alternaria tenuis*), Cercospora leaf blotch (*Mycovellosiella concors, Cercospora concors, Cercospora solani, Cercospora solani-tuberosi*), Charcoal rot (*Macrophomina phaseolina, Sclerotium bataticola*), Choanephora blight (*Choanephora cucurbitarum*), Common rust (*Puccinia pittieriana*), Deforming rust (*Aecidium cantensis*), Early blight (*Alternaria solani*), Fusarium dry rot (*Fusarium* spp. *Gibberella pulicaris, Fusarium solani*; Other *Fusarium* spp. include: *Fusarium avenaceum, Fusarium oxysporum, Fusarium culmorum*; less common *Fusarium* spp. include: *Fusarium acumination, Fusarium equiseti, Fusarium crookwellense*), Fusarium wilt (*Fusarium* spp. *Fusarium avenaceum, Fusarium oxysporum, Fusarium solani* f.sp. *eumartii*), Gangrene (*Phoma solanicola* f. *foveata, Phoma foveata, Phoma exigua* var. *foveata, Phoma exigua* f. sp. *Foveata, Phoma exigua* var. *exigua*), Gray mold (*Botrytis cinerea, Botiyotinia fuckeliana* [teleomorph]) Late blight (*Phytophthora infestans*), Leak (*Pythium* spp. *Pythium ultimum* var. *ultimum, Pythium debaiyanum, Pythium aphanidermatum, Pythium deliense*), Phoma leaf spot (*Phoma andigena* var. *andina*), Pink rot (*Phytophthora* spp. *Phytophthora czyptogea, Phytophthora drechsleri, Phytophthora erythroseptica, Phytophthora megasperma, Phytophthora nicotianae* var. *parasitica*), Powdery mildew (*Ezysiphe cichoracearum*), Powdery scab (*Spongospora subterranea* f.sp. *subterranean*), Rhizoctonia canker and black scurf (*Rhizoctonia solani, Thanatephorus cucumeris* [teleomorph]), *Rosellinia* black rot (*Rosellinia* sp. *Dematophora* sp. [anamorph]), *Septoria* leaf spot (*Septoria lycopersici* var. *malagutii*), Silver scurf (*Helminthosporium solani*), Skin spot (*Polyscytalum pustulans*), Stem rot (southern blight) (*Sclerotium rolfsii, Athelia rolfsii* [teleomorph]), *Thecaphora* smut (*Angiosorus solani, Thecaphora solani*), Ulocladium blight (*Ulocladium atrum*), Verticillium wilt (*Verticillium alboatrum, Verticillium dahlia*), Wart (*Synchytrium endobioticum*), and White mold (*Sclerotinia sckrotiorum*), etc.

II) Bacterial diseases that can be addressed or treated as described herein include but are not limited to: Bacterial wilt (brown rot) caused by *Ralstonia solanacearum* (*Pseudomonas solanacearum*); Blackleg and bacterial soft rot caused by *Pectobacterium carotovorum* subsp. *Atrosepticum, Envinia carotovora* subsp. *Atroseptica, Pectobacterium carotovorum* subsp. *Carotovorum, E. carotovora* subsp. *Carotovora, Pectobacterium chrysanthemi, E. chrysanthemi*; Pink eye caused by *Pseudomonas fluorescens*; Ring rot caused by *Clavibacter michiganensis* subsp. *Sepedonicus, Corynebacterium sepedonicum*; Common scab caused by *Streptomyces scabiei, S. scabies, Streptomyces acidiscabies, Streptomyces turgidiscabies*); and, etc.

There are a number of benefits which accrue using the compounds as described herein, examples of which include:

1. Increased potato firmness leads to reduced pressure bruising which in turn leads to better storability of potato tubers especially for the long term. Maintenance of desirable potato pile height (due to decreased softening and flaccidity so that the space between potatoes, the interstices, are more effectively maintained) results in better air circulation, better disease control and management, better distribution of sprout control products leading to improved efficacy.
2. Maintains high water content in potato tubers and reduces moisture loss leading to more desirable lower potato bulk density. Settled piles have smaller volume of air spaces between the potatoes, by increasing the contact area between potatoes leading to less air movement and contribute to conditions conducive to disease development.
3. Restores normal water content in potato tubers which have been desiccated due to sprouting or other reasons and reduces overall moisture loss leading to more desirable lower potato bulk density.
4. For processing and fresh market potatoes, turgid, firm or hard potatoes provide better slicing (for chips and the like) and have better peeling characteristics
5. Farmers store potatoes in boxes or crates or smaller pile heights to avoid pressure bruising. Compounds can reduce the cost of storage by resorting to a more cost-effective method of storing in large piles. This can be of significant economic benefit.
6. Turgid, firm or hard tubers can be better transported without causing skin injury and thereby the possibility of secondary disease infestation is reduced.
7. Turgid, firm or hard tubers benefit from a longer shelf life (i.e., last longer in the kitchen pantry or on the grocery shelf)
8. Turgid, firm or hard tubers which have been treated with such compounds also exhibit lower incidence of greening both in storage as well as in kitchen pantries.
9. Turgid, firm or hard tubers give higher rates of packout by reducing "shrinkage"—the loss of the overall weight of the stored potatoes and discarded potatoes (due to greening) leading to a higher economic return for the farmer
10. Turgid or hard tubers are aesthetically pleasing and can therefore more saleable and can command a better price (especially for fresh market potatoes).
11. Turgid or hard tubers are easier to unload from the storage with conventional unloading equipment. Non-turgid or soft tubers can be subject to heavy damage. Soft tubers do not roll easily on conveyer belts or machinery designed to mechanically remove, transport, wash and pack potatoes.

EXAMPLES

Example 1

An exemplary sprout inhibitor is marketed in the USA under the tradename SmartBlock® and it includes as its active ingredient, 3-decen-2-one, an alpha-beta unsaturated ketone. SmartBlock® was applied to potatoes in a commercial storage facility in Idaho. Since these tubers were destined for the processing market, storage temperatures of e.g. 46 to 48 deg F. would have been generally recommended to lower the content of reducing sugars. However, this particular storage was maintained at a higher temperature, with the temperature probe within the potato pile reading 52 deg F. While the storage was maintained at a high relative humidity (approximately 95% RH), which is generally recommended under such conditions, high RH usually does very little to sprouting and reverse moisture loss. At the time of treatment, well over 90% of the potatoes were sprouted, with average sprouts being 2 to 4 inch (5 to 10 cm) in length, with some sprouts being as long as 10 inches (25 cm) (see FIG. 1A). The application of SmartBlock® "burnt off" the sprouts (see FIG. 1B).

Figure 1:
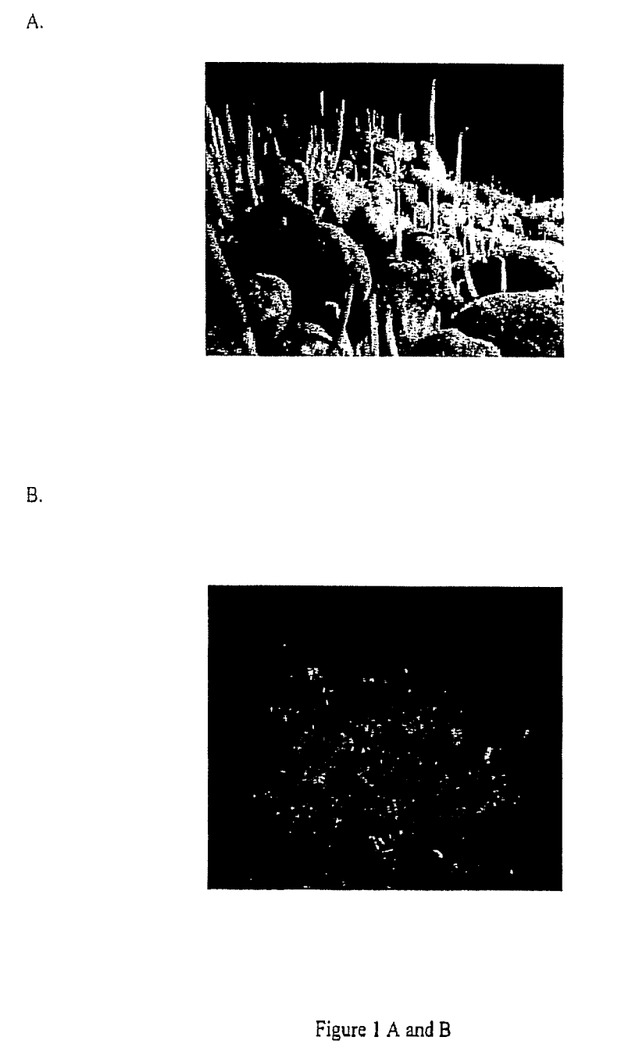

The excessive sprouting illustrated in FIG. 1 had caused the potato tubers to also lose moisture quite rapidly causing them to wrinkle and shrivel and leading to significant weight loss and settling of the potato pile. It would be expected that heavily sprouted tubers would, even after the sprouts were removed, still continue to show a loss of turgidity and weight due to desiccation after removal from storage. However, 14 days after the SmartBlock® treatment, when the potato tubers were being monitored for sprout control and quality (including sugar levels), it was surprisingly and unexpectedly noted that the potato tubers were noticeably more turgid (hard or firm to the touch) than would normally be expected for tubers which were heavily sprouted, even after removal of sprouts. Instead of soft (flaccid), wrinkly or otherwise shriveled potatoes, it was observed that the tubers were very hard or firm to the touch and could be cut, diced or sliced easily.

Figure 2:
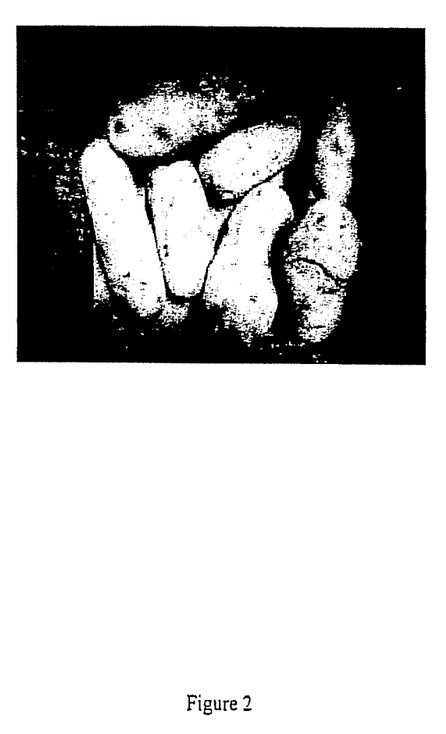
FIG. 2 is a photograph of unwashed potato tubers twenty one (21) days after sampling, thirty five (35) days after treatment with the exemplary agent 3-decen-2-one.
Figure 3A:
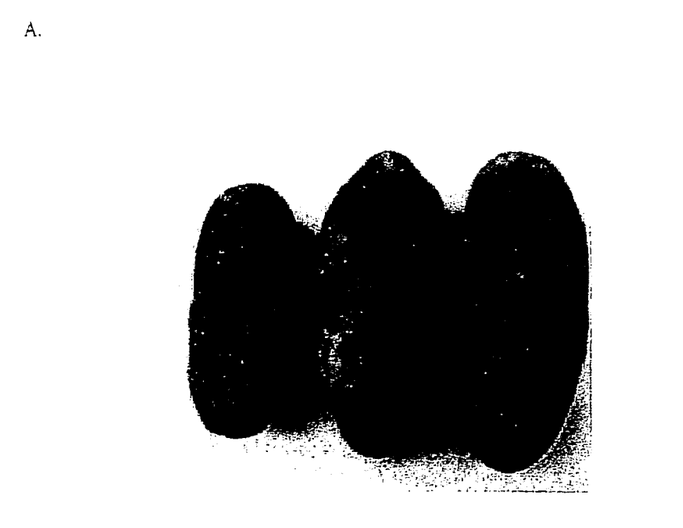
FIGS. 3A and B depicts some of the potato tubers of FIG. 2 after a shelf life study, in unwashed (A) and washed (B) condition FIGS. 4A and B. Treatment of tubers infected with *Fusarium* dry rot. A, untreated control to tubers; B, tubers treated with 3-decen-2-one.
Figure 3B:
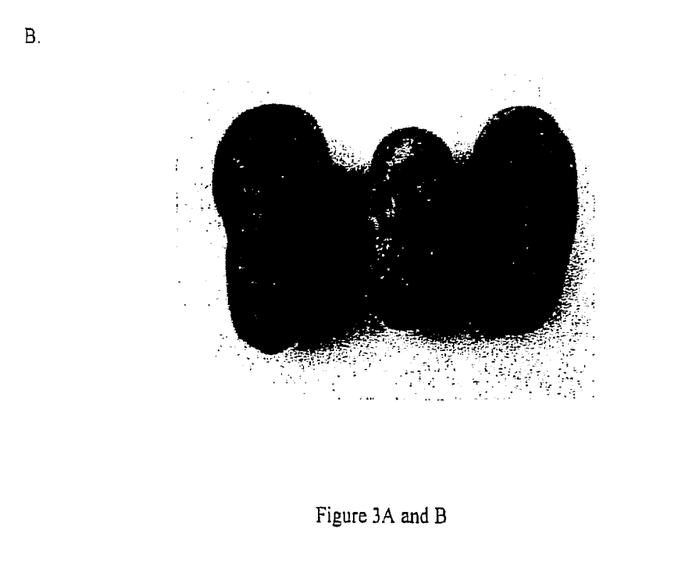

The sampled potatoes were then subject to a sprouting shelf-life study. The objective of the study was to observe if the turgidity could be maintained over time after removal from storage. SmartBlock® was applied at 115 g/ton on April 16 using commercial thermal fogging equipments. Samples of the potatoes from which the sprouts had been removed by this treatment were collected. Some were washed and some remained unwashed, and all tubers were stored in a cardboard box on a kitchen counter at room temperature (approximately 70 deg F.), beginning on April 29 (see FIG. 2). The turgidity and appearance of the potatoes were monitored. As can be seen from FIGS. 3A and B, both washed and unwashed tubers did not exhibit the normal loss of turgidity and that would be expected, even when exposed to light for over 14-21 days. This result was highly unexpected as sprouted potatoes are known to continue to lose turgidity even after sprouts are removed. Significantly, the tubers also did not exhibit typical greening or a recurrence of sprouting. Qualitatively, the tubers remained fully turgid to the touch and only suffered minor softening by day 21 (See Table 1).

These results show that the turgiditiy of flaccid potatoes can be restored by application of 3-decen-2-one or related compounds. In addition, application of 3-decen-2-one can prevent or treat greening in potatoes.

TABLE 1

Observations on Samples after Commercial Treatment with SmartBlock ®

| Date | Sample # | # of Eyes On Tuber | # of Blackened Eyes | % Blackened | % Average of 3 Tubers | Observations |
|---|---|---|---|---|---|---|
| Washed tubers | | | | | | |
| 29-Apr | 1 | 23 | 23 | 100 | | |
| | 2 | 27 | 27 | 100 | | |
| | 3 | 23 | 23 | 100 | 100 | All 3 tubers were hard and showed no loss in turgidity, no greening or sprouting |
| 6-May | 1 | 23 | 23 | 100 | | |
| | 2 | 27 | 27 | 100 | | |
| | 3 | 23 | 23 | 100 | 100 | All 3 tubers were hard and showed no loss in turgidity, no greening or sprouting |
| 11-May | 1 | 23 | 23 | 100 | | |
| | 2 | 27 | 27 | 100 | | |
| | 3 | 23 | 23 | 100 | 100 | All 3 tubers were hard and showed no loss in turgidity, no greening or sprouting |
| 19-May | 1 | 23 | 22 | 95.4 | | |
| | 2 | 27 | 25 | 92.6 | | |
| | 3 | 23 | 23 | 100 | 96 | All 3 tubers were hard and showed minimal loss in turgidity. Greening in ⅓ tubers. Some "peeping" (eyes opening) |

TABLE 1-continued

Observations on Samples after Commercial Treatment with SmartBlock ®

| Date | Sample # | # of Eyes On Tuber | # of Blackened Eyes | % Blackened | % Average of 3 Tubers | Observations |
|---|---|---|---|---|---|---|
| | | | Unwashed tubers | | | |
| 29-Apr | 1 | 22 | 22 | 100 | | |
| | 2 | 24 | 24 | 100 | | |
| | 3 | 26 | 26 | 100 | 100 | All 3 tubers were hard and showed no loss in turgidity, no greening or sprouting |
| 6-May | 1 | 22 | 22 | 100 | | |
| | 2 | 24 | 24 | 100 | | |
| | 3 | 26 | 26 | 100 | 100 | All 3 tubers were hard and showed no loss in turgidity, no greening or sprouting |
| 11-May | 1 | 22 | 22 | 100 | | |
| | 2 | 24 | 24 | 100 | | |
| | 3 | 26 | 26 | 100 | 100 | All 3 tubers were hard and showed no loss in turgidity, no greening or sprouting |
| 19-May | 1 | 22 | 21 | 95.4 | | |
| | 2 | 24 | 23 | 95.4 | | |
| | 3 | 26 | 24 | 92.3 | 94.5 | All 3 tubers were hard and showed minimal loss in turgidity. No greening. Some sprouting (<0.5 cm) |

Example 2

The source of tubers for this study was Telford Farms in Paul, Id. The storage unit temperature set point was 48.5° F. (9° C.). The tuber pulp temperatures ranged from 49 to 53.6° F. (9 to 12° C.) depending upon their location in the pile. Untreated tubers (cv Alturas) were selected from storage on Jul. 2, 2013 (prior to SmartBlock® application) to serve as untreated controls. About 200 lbs (91 kg) of these were distributed into 4 coolers with cold packs and transported to the Fed Ex office in Twin Falls, Id. at 1:45 pm where they remained in the air conditioned office until 6:23 pm when they left the facility. Untreated tubers to arrived in Pullman at 11:45 am on July 3.

SmartBlock® was applied at a rate of 4.2 fluid oz ton$^{-1}$ (136 mL MT$^{-1}$) to tubers remaining in the Telford Farms storage on July 2. Ventilation was suspended for an estimated 12 to 18 hrs. post treatment. A shipment of the treated tubers was packed as described above and delivered to Fed Ex in Twin Falls for shipment on July 3. The shipment arrived in Pullman on July 5 at 11:30 am.

Tubers were sorted into weight categories immediately upon arrival in Pullman, working at room temperature (~25° C.) and in dim light (0.16-1.34 µE sec$^{-1}$ m$^{-2}$). Two experimental groups were created from the untreated (control) tubers; those with one or more sprouts ≥0.5 cm and those with no significant (>2 mm) sprouts. Sorting of tubers and their assignment to treatment groups for the various experiments was accomplished within 1.5 hr. and subsequently all tubers were placed in dark, walk-in storage at 8° C. with 85 to 90% RH. Humidity was maintained through the use of a household room humidifier, water on the concrete floor, and damp burlap placed on the empty shelves.

Measuring Tuber Firmness:

Tubers for firmness measurements were sorted by treatment and blocked for size. Each treatment group (containing at least 24 tubers) was stored in a plastic tote in the walk-in cold room at 8° C. Damp burlap was placed atop the tote so as not to contact the tubers directly. Burlap was re-wetted every two days. At 6, 13, 20, and 27 days after treatment (DAT), six tubers from each rep of each treatment (3-decen-2-one-treated and non-treated not sprouted) were selected and gently rinsed under cold running water to remove surface soil. The tubers were placed in plastic tubs and covered with damp paper towels for transport to the testing facility.

A TA-XT-2 texture analyzer (Stable Microsystems) was used to test tubers for firmness. A section of peel was removed from the midsection on opposite sides of the tuber. An 8-mm probe was lowered into the tuber tissue within this peeled area to a distance of 5 mm at a speed of 1 mm s$^{-1}$. Firmness was recorded as the N (m kg s−1) required to achieve the specified penetration. The two readings per tuber were averaged. Analysis of variance was performed on the data set. The results are presented in Table 2.

TABLE 2

Firmness of SmartBlock ® - treated and non-treated tubers (cv Alturas) as measured with a TA-XT-2 texture analyzer. Tubers were stored at 8° C. until analysis. Data are presented as Newtons (N) required to force a 8-mm probe to a depth of 5 mm into the tuber flesh at 1.0 mm s$^{-1}$. Data are the means of 6 tubers.

| Treatments | Days after Treatment | Rep 1 | Rep 2 | Rep 3 | Rep 4 | Average | % Increase |
|---|---|---|---|---|---|---|---|
| 3-decen-2-one (115 ppm) | 6 | 67.84 | 79.18 | 75.64 | 78.85 | 75.38 | 4.09 |
| untreated | | 66.04 | 78.44 | 71.61 | 73.58 | 72.42 | |
| 3-decen-2-one (115 ppm) | 13 | 73.22 | 67.34 | 73.98 | 79.26 | 73.45 | 2.80 |
| untreated | | 69.46 | 71.47 | 70.62 | 74.26 | 71.45 | |
| 3-decen-2-one (115 ppm) | 20 | 74.51 | 74.63 | 72.81 | 77.64 | 74.90 | 3.28 |
| untreated | | 73.20 | 70.66 | 69.77 | 76.36 | 72.52 | |

Results: The increase in tuber firmness is of significant commercial value because as the potatoes lose turgidity over time due to moisture loss in storage, the risk of pressure bruising is increased (stacking weight of the potatoes damage or bruise potatoes lower in the potato pile), lower air circulation (which increases the risk of disease development, and causes a rise in sugar levels due to tuber stress) and internal sprouting (sprouts turn inside the tuber), leading to destruction of tuber quality. Therefore, even a slight increase in turgidity can have a significant commercial impact on tuber quality.

Example 3

Diseases which develop during storage of potatoes include dry rot (*Fusarium sambucinum*), common scab (*Streptomyces* spp, pink rot (*Phytopthora erythoseptica*) late blight (*Phytopthora infestans*), black scurf (*Rhizoctonia* spp), *Pythium* leak (*Pythium* spp), silver scurf (*Helminthosporium solani*), etc. Such diseases are often very difficult to control inside a storage facility. Many of the diseases are due to infections acquired in the field and are exacerbated by potato wounds that occur during harvesting operations. The rate of spread within a storage container depends on conditions such as temperature, humidity, ventilation, etc. Typically, certain fungicides are applied in storage to combat disease development, but they have the drawback that they cannot be easily dispersed into the pile. Therefore, a chemical which can be applied by fogging (e.g. cold fog, hot fog, vapor etc.) and which possesses the property of arresting further development of such diseases would be of tremendous commercial value.

Suberization of the skin of the potato is critical to arresting the spread of fungi and bacteria. Suberization acts by "sealing up" the diseased sector and preventing further spread inside the tuber or outside to adjacent tubers (see picture B, the affected and sealed region is indicated with a circle on the whole potato). By "sealing up" the infected site, the integrity of the potato is maintained, thereby preventing the rapid spread of disease throughout the potato or vegetable pile. Agents that facilitate this process would be of great benefit.

Essential oils and other molecules related to saturated and alpha-beta unsaturated ketones and aldehydes are known to have some fungicidal properties but these compounds were previously thought to be active against infectious agents at the surface of the tuber. The data presented in this Example shows that, surprisingly, these type of compounds can also arrest the development of fungi or bacteria inside the tuber and not just on the surface of potatoes. In so doing, the compounds appear to support or induce suberization. As shown below, application of these compounds can significantly reduce (e.g. up to about 70% or greater) the overall incidence of diseases in the tuber.

Data: Potatoes stored commercially in Taber, Alberta, Canada had a heavy infestation of predominantly dry rot (*Fusarium sambucinum*) prior to treatment. The potatoes were observed to be "wet" due to the fungal mycelia and deterioration of the potato skin. The tubers also exhibited heavy sprouting (sprouts up to 2.5 cm long).

Figure 4A:
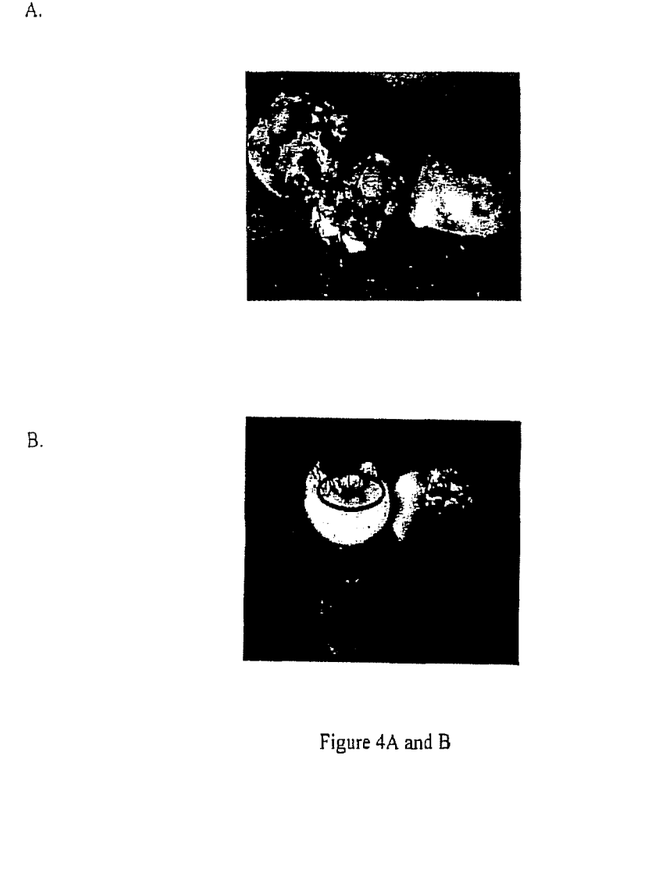

One group of sprouted, diseased tubers (Storage Bin 3) were treated with 3-decen-2-one (as SmartBlock®) at the rate of 115 ppm using a hot fogging method. Another group of tubers was left untreated as a control. The results of the test are shown in FIGS. 4A and B and Table 3. As can be seen, treatment with 3-decen-2-one (FIG. 4B) not only reduced/prevented sprouting, but also decreased or eliminated symptoms of dry rot, compared to untreated controls (FIG. 4A).

TABLE 3

Performance of 3-decen-2-one in a commercial storage in Canada. Disease defects (indicated as total defects) in Storage Bin 3: Potato variety FL 2053

| Date | % Total Defects | Change | Notes |
|---|---|---|---|
| Oct. 12, 2013 | 3.15 | N/A | Bin loaded on Sep. 29, 2013 |
| Oct. 30, 2013 | 12.2 | +287.3 | Fusarium rot disease is progressing rapidly. |
| Nov. 13, 2013 | 14.30 | +17.2 | Fusarium rot continues to increase. Sprouting of tubers is serious |
| Nov. 13, 2013 | Same | Same | 3-decen-2-one was applied to Bin 3 at 115 ppm as a thermal fog/vapor to control sprouts |
| Dec. 10, 2013 | 4.23 | -70.4 | Bin was unloaded on Dec. 10 (3-weeks after treatment) and tubers were shipped to an international potato processing facility where final grading of the tubers was done as part of routine quality control. Sprout control was excellent but in addition, the tubers were not moist and mold development had been arrested. |

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of reversing symptoms of a fungal or bacterial disease within potato tubers, comprising the step of applying to harvested or stored potato tubers, a composition consisting of 3-decen-2-one in an amount that is sufficient to reverse symptoms of said fungal or bacterial disease within the potato tubers, wherein said fungal or bacterial or disease is *Fusarium* dry rot.

2. The method of claim 1 wherein said step of applying is performed by fogging or vaporizing.

3. The method of claim 1, wherein said harvested or stored potato tubers exhibit symptoms of one or more fungal or bacterial diseases prior to said step of applying.

* * * * *